US012629448B2

(12) United States Patent
Xu et al.

(10) Patent No.: US 12,629,448 B2
(45) Date of Patent: May 19, 2026

(54) PREPARATION METHOD FOR THREE-DIMENSIONAL GELATIN SCAFFOLD WITH INTERCONNECTED PORES AND APPLICATION THEREOF

(71) Applicant: Tianjin Hospital, Tianjin (CN)

(72) Inventors: Baoshan Xu, Tianjin (CN); Tongxing Zhang, Tianjin (CN); Tong Li, Tianjin (CN); Zhenhua Li, Tianjin (CN); Haifan Zhao, Tianjin (CN); Bing Peng, Tianjin (CN); Jianhai Wang, Tianjin (CN)

(73) Assignee: Tianjin Hospital, Tianjin (CN)

( * ) Notice: Subject to any disclaimer, the term of this patent is extended or adjusted under 35 U.S.C. 154(b) by 0 days.

(21) Appl. No.: 18/991,280

(22) Filed: Dec. 20, 2024

(65) Prior Publication Data

US 2025/0121115 A1     Apr. 17, 2025

(30) Foreign Application Priority Data

May 8, 2024     (CN) .......................... 202410558756.1

(51) Int. Cl.
 *A61L 27/22*          (2006.01)
 *A61L 27/36*          (2006.01)
 *A61L 27/56*          (2006.01)

(52) U.S. Cl.
 CPC ......... *A61L 27/222* (2013.01); *A61L 27/3604* (2013.01); *A61L 27/56* (2013.01); *A61L 2430/34* (2013.01)

(58) Field of Classification Search
 None
 See application file for complete search history.

(56) References Cited

U.S. PATENT DOCUMENTS 5,958,451 A * 9/1999 Chen .................... A61K 9/4825
                                                        424/452
2018/0250437 A1* 9/2018 Baer ........................ A61L 27/56
2021/0236697 A1* 8/2021 Huang ................ A61L 27/3687

FOREIGN PATENT DOCUMENTS

CN          106176579 A     12/2016
CN          106620849 A  *  5/2017  ............. A61L 27/26
KR       20130091824 A      8/2013

OTHER PUBLICATIONS

Machine translation of CN 106620849 A. (Year: 2017).*

(Continued)

*Primary Examiner* — Carlos A Azpuru
*Assistant Examiner* — Casey S Hagopian

(57)          ABSTRACT

The present application provides a preparation method for a three-dimensional gelatin scaffold with interconnected pores and an application thereof. The preparation method includes the steps of: dissolving a pharmaceutical gelatin to obtain a gelatin solution; emulsifying the gelatin solution using an ultrasonic crusher to obtain a gelatin emulsion; pouring the gelatin emulsion into a preset mold, and freezing and curing the gelatin emulsion to obtain a cured product; performing vacuum drying of the cured product using a low-temperature freeze dryer to obtain a dried product; cross-linking and denaturing the dried product with glutaraldehyde to obtain a cross-linked product; and washing the cross-linked product several times, followed by freeze-drying to obtain a three-dimensional gelatin scaffold with interconnected pores. The three-dimensional gelatin scaffold with interconnected pores has an optimal pore size, porosity and pore size of inter-connected pores, and the preparation method is applicable to industrial production.

1 Claim, 9 Drawing Sheets

(56)        References Cited

OTHER PUBLICATIONS

Rose et al. "Gelatin-Based Materials in Ocular Tissue Engineering", Materials, 2014, 7(4), pp. 3106-3135. (Year: 2014).*

Silva et al. "Sonication technique to produce emulsions: The impact of ultrasonic power and gelatin concentration", Ultrasonics Sonochemistry, vol. 52, 2019, pp. 286-293. (Year: 2019).*

Reys et al. "Influence of freezing temperature and deacetylation degree on the performance of freeze-dried chitosan scaffolds towards cartilage tissue engineering", European Polymer Journal, vol. 95, Oct. 2017, pp. 232-240. (Year: 2017).*

Standard Intelligent Ultrasonic cell crusher. Laboao. Accessed online on Feb. 28, 2025 at https://www.laboao.com/. (Year: 2025).*

Zeng et al. "Bone Marrow Mesenchymal Stem Cells in a Three-Dimensional Gelatin Sponge Scaffold Attenuate Inflammation, Promote Angiogenesis, and Reduce Cavity Formation in Experimental Spinal Cord Injury". Cell Transplantation, vol. 20, Issue 11-12, Dec. 2011, pp. 1881-1899. (Year: 2011).*

Yang et al. "Assessment of the characteristics and biocompatibility of gelatin sponge scaffolds prepared by various crosslinking methods", Scientific Reports , vol. 8, Article No. 1616 (2018), pp. 1-13. (Year: 2018).*

\* cited by examiner

Gelatin solution

Preparation of gelatin emulsion

Mold

Inoculation of cells

Three-dimensional gelatin scaffold with interconnected pores

Freeze-drying

PREPARATION METHOD FOR THREE-DIMENSIONAL GELATIN SCAFFOLD WITH INTERCONNECTED PORES AND APPLICATION THEREOF

CROSS-REFERENCE TO RELATED APPLICATION

This application claims priority of Chinese Patent Application No. 202410558756.1, filed on May 8, 2024, the entire contents of which are incorporated herein by reference.

TECHNICAL FIELD

The present application relates to the technical field of biomedical materials, and especially to a preparation method for a three-dimensional gelatin scaffold with interconnected pores and an application thereof.

BACKGROUND

Tissue defects in skin, muscles, bones, and intervertebral discs are common in clinical. Therefore, how to achieve effective regeneration and repair of tissue defects is a medical problem urgently to be solved. The advancement of biomaterials and regenerative medicine is of great help to the regeneration and repair of tissue defects, and research has proved that biomaterials can provide a good platform for the regeneration and repair of tissue defects. As the regenerative medicine develops, the combination of biomaterials and stem cells shows great potential for repairing tissue defects.

However, many factors affect the growth of stem cells on biomaterial scaffold, and the cell growth space, which depends on the pore size and porosity of the scaffold as well as the interconnectivity of pores, is crucial to cell growth and metabolism. Large pores boost the nutrients delivery and cell differentiation, and interconnected small pores are beneficial for intracellular signal transmission and intercellular interactions. In terms of the porosity, excessively large porosity is prone to collapsing structure of the scaffold, and excessively small porosity or interconnected pores is unfavorable for cell growth and migration in the scaffold. Different cells can grow well on materials with different pore sizes, porosities, and interconnected pores, but there is no unified view on the pore size, porosity, and interconnected pores that are suitable for stem cell adhesion and proliferation.

In response to this, the present application proposes a new preparation method to change the pore size, porosity, and interconnected pores of biomaterial scaffold, preparing a novel three-dimensional gelatin scaffold with interconnected pores having a pore size, porosity, and interconnected pores most suitable for loading stem cells, thereby providing a new strategy for tissue defect repair.

SUMMARY

The present application provides a preparation method for a three-dimensional gelatin scaffold with interconnected pores and an application thereof to solve the above problems.

In a first aspect, an embodiment of the present application provides a preparation method for a three-dimensional gelatin scaffold with interconnected pores, including:

step 1: dissolving a pharmaceutical gelatin using a water bath heating method to obtain a gelatin solution at a preset concentration;

step 2: emulsifying the gelatin solution using an ultrasonic crusher to obtain a gelatin emulsion;

step 3: pouring the gelatin emulsion into a preset mold, and freezing and curing the gelatin emulsion at −80° C. after being stabilized for a preset time, to obtain a cured product;

step 4: performing vacuum drying of the cured product using a low-temperature freeze dryer to obtain a dried product;

step 5: cross-linking and denaturing the dried product with glutaraldehyde to obtain a cross-linked product; and step 6: washing the cross-linked product several times, followed by freeze-drying to obtain a three-dimensional gelatin scaffold with interconnected pores.

In an alternative embodiment of the present application, in step 1, a Bloom strength of the pharmaceutical gelatin is 250 Bloom/g, and the preset concentration of the gelatin solution ranges from 2 wt % to 10 wt %.

In an alternative embodiment of the present application, in step 2, time for emulsifying the gelatin solution using the ultrasonic crusher is 30 s, and an ultrasonic power of the ultrasonic crusher is 200 W.

In an alternative embodiment of the present application, in step 3, a preset time for stabilizing the gelatin emulsion ranges from 1 min to 4 min.

In an alternative embodiment of the present application, in step 3, time for the freezing and curing ranges from 3 h to 6 h.

In an alternative embodiment of the present application, in step 4, a vacuum strength for vacuum drying of the cured product using the low-temperature freeze dryer is not greater than 10 Pa, and vacuum drying time ranges from 24 h to 72 h.

In a second aspect, an embodiment of the present application provides an application of a three-dimensional gelatin scaffold with interconnected pores in preparing a scaffold for tissue defect repair, a three-dimensional gelatin scaffold with interconnected pores being obtained by a preparation method mentioned in the first aspect, and the three-dimensional gelatin scaffold with interconnected pores being used as a carrier for stem cells for repairing tissue defects.

In an alternative embodiment of the present application, the stem cells include adipose-derived mesenchymal stem cells, bone marrow mesenchymal stem cells or umbilical cord mesenchymal stem cells.

In an alternative embodiment of the present application, the three-dimensional gelatin scaffold with interconnected pores is cut into different shapes and sizes for generation and repair of tissue defects of different shapes.

In an alternative embodiment of the present application, the three-dimensional gelatin scaffold with interconnected pores has a pore size ranging from 70 μm to 450 μm, a porosity ranging from 64.2% to 97.7%, and a pore size of interconnected pores ranging from 30 μm to 185 μm.

The present application includes the following advantages: the present application provides a preparation method for a three-dimensional gelatin scaffold with interconnected pores and an application thereof. A pharmaceutical gelatin is dissolved using a water bath heating method to obtain a gelatin solution at a preset concentration; the gelatin solution is emulsified using an ultrasonic crusher to obtain a gelatin emulsion; the gelatin emulsion is poured into a preset mold, and the gelatin emulsion is frozen and cured at −80° C. after being stabilized for a preset time, to obtain a cured product; vacuum drying is performed on the cured product using a low-temperature freeze dryer to obtain a dried product; the dried product is cross-linked and denatured with glutaraldehyde to obtain a cross-linked product; and the cross-linked product is washed several times, followed by freeze-drying to obtain a three-dimensional gelatin scaffold with interconnected pores. The three-dimensional gelatin scaffold with interconnected pores, which has an optimal pore size and porosity, can be obtained by the preparation method. The preparation method is simple, stable and efficient, and is applicable to industrial production. The novel three-dimensional gelatin scaffold with interconnected pores prepared in the present application has pore size, porosity, and interconnected pores that are appropriate for stem cell loading, shows excellent hemostatic properties, and is suitable as a platform for loading adipose-derived mesenchymal stem cells for the regeneration and repair of tissue defects.

BRIEF DESCRIPTION OF THE DRAWINGS

To state the technical solutions of the embodiments in the present application clearer, the attached drawings needed in the description of the embodiments are briefly introduced below. Obviously, the drawings described below are merely some embodiments in the present application, and for those ordinary skilled in the art, other drawings can be obtained according to these drawings without creative efforts.

DETAILED DESCRIPTION

Figure 1:
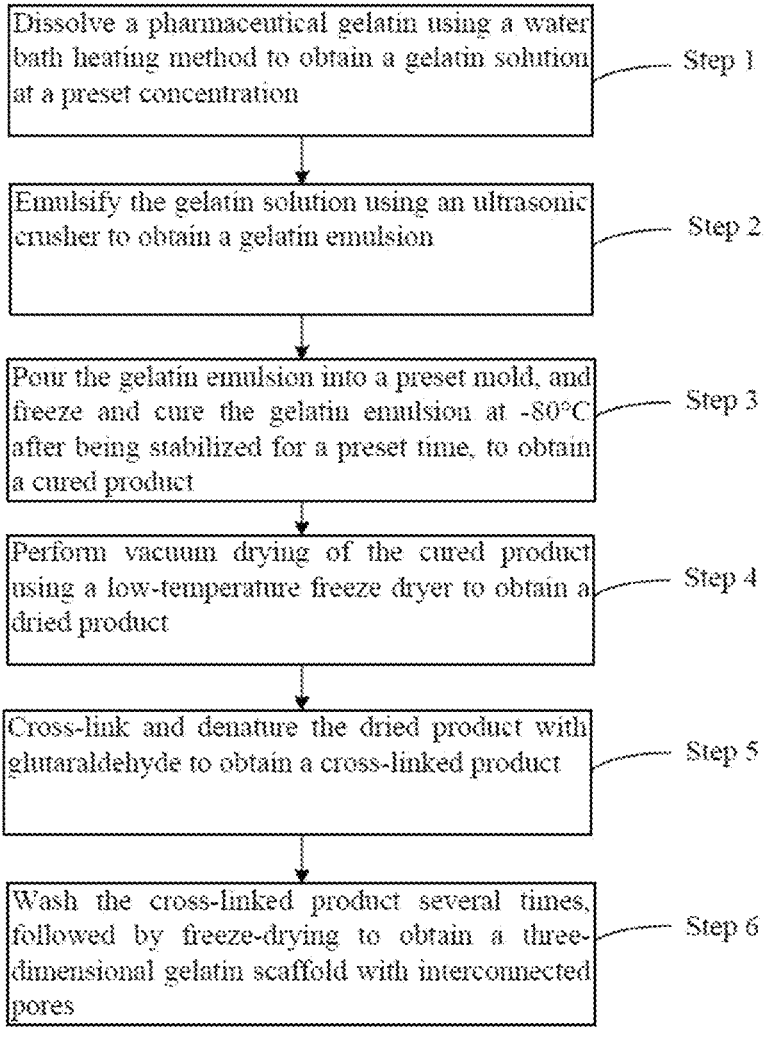
FIG. 1 is a flow chart showing steps of a preparation method for a three-dimensional gelatin scaffold with interconnected pores according to an embodiment of the present application.

The technical solutions of the embodiments in the present application will be described clearly and completely by reference to the attached drawings of the embodiments in the present application below. Obviously, the embodiments described are only some, rather than all embodiments of the present application. On the basis of the embodiments of the present application, all other embodiments obtained by those ordinary skilled in the art without creative efforts fall within the scope of protection of the present application.

Tissue defects in skin, muscles, bones, and intervertebral discs are common in clinical. Therefore, how to achieve effective regeneration and repair of tissue defects is a medical problem urgently to be solved. The advancement of biomaterials and regenerative medicine is of great help to the regeneration and repair of tissue defects, and research has proved that biomaterials can provide a good platform for the regeneration and repair of tissue defects.

Currently, biomaterials used for tissue defect repair include synthetic biomaterials and natural biomaterials. Synthetic biomaterials, formed by artificially processing and synthesizing different substances, are widely used as tissue fillers due to their low cost, good mechanical properties, and excellent controllability. However, the synthetic biomaterials have a relatively poor affinity for tissues, and their degradation products pose a risk of causing chronic inflammation, making many synthetic biomaterials difficult to be translated in clinical practice. Natural biomaterials, i.e., substances inherent to living organisms, are well adapted in living organisms because of their intrinsic chemical composition and unique functionality. Natural biomaterials boast superior cytocompatibility, biodegradability, and low immunogenicity. Moreover, they possess adjustable mechanical properties, and can serve as an advantageous physical platform to ensure tissue reconstruction and resistance to changes in stress. Therefore, as tissue engineering develops, the natural biomaterials are gradually becoming the preferred choice as tissue fillers.

Currently, natural biomaterials used as tissue fillers mainly include gelatin, hyaluronic acid, chitosan, sodium alginate and dextrose, etc. Gelatin is derived from collagen, which has similar physicochemical properties and biocompatibility with collagen, and has been widely applied in clinical practice due to its ease of extraction, low economic cost and biodegradability. Gelatin, as one of the few natural materials that have been applied in human body, has been widely used in pharmaceutical and medical fields, such as hemostatic agents, embolic agents and drug carriers, especially in the preparation of hemostatic agents, and the hemostatic effect involves the promotion of platelet aggregation and the adsorption of coagulation factors. Additionally, it has been proved that gelatin has a high affinity to red blood cells, beneficial to the formation of thrombus and hemostasis. Due to its low cost and easy accessibility, gelatin is commonly available commercially in various forms of hemostatic products, such as nanoparticles, hydrogels, foams and sponges. Commercial gelatin, in particular, has a fluffy structure and a large number of large pores, having certain advantages over other forms of hemostatic materials.

Gelatin sponges can expand after absorbing blood, and are able to absorb blood equivalent to several times their own weight, compressing the surrounding area and providing good hemostasis. Accordingly, gelatin has become an indispensable hemostatic material in emergency treatment, trauma, general surgery and other surgical fields.

As the regenerative medicine develops, the combination of biomaterials and stem cells has shown great potential for repairing tissue defects. All relevant studies hope to change the microstructure and properties of gelatin materials by improving their preparation methods, so as to enhance the adhesion and growth of stem cells on the surface and inside of biomaterials. Although loading cells by gelatin sponge still risk many clinical problems and challenges, with the cross-integration of disciplines such as cytology, molecular biology and biomaterials, the combined repair scheme of gelatin sponge and stem cells make the regenerative repair of tissue defects possible. However, there are many factors affecting the growth of stem cells on gelatin sponges. Excessively large pores are not conducive to cell growth and differentiation, and the cell growth space is crucial to cell growth and metabolism. The cell growth space depends on the pore size and porosity of the scaffold material as well as the interconnected pores. It is reported that large pores boost the nutrients delivery and cell differentiation, and interconnected small pores are beneficial for intracellular signal transmission and intercellular interactions. In terms of the porosity, excessively large porosity is prone to collapsing structure of the material, and excessively small porosity or interconnected pores is unfavorable for cell growth and migration in the material. Different cells require different pore sizes, porosities, and interconnected pores to grow well, but there is no unified view on the pore size, porosity, and interconnected pores that are optimal for stem cell adhesion and proliferation.

In summary, gelatin material possesses strong clinical applicability, and its microstructure can be controlled by changing the preparation method, and the commercial gelatin material currently used in clinical application mainly serves as hemostatic material. To expand the medical application scope of gelatin materials, a series of novel three-dimensional gelatin scaffolds with interconnected pores having different pore sizes, porosities, and interconnected pores are prepared using gelatin materials, and the novel three-dimensional gelatin scaffold with interconnected pores suitable for the adhesion and growth of adipose-derived mesenchymal stem cells is explored through in vitro adipose-derived mesenchymal stem cells loading experiments, determining the preparation process for the novel three-dimensional gelatin scaffold with interconnected pores having the pore size, porosity, and interconnected pores most suitable for loading stem cells, providing theoretical support for the clinical translation of the novel three-dimensional gelatin scaffold with interconnected pores as stem cell carrier, and thus providing a new strategy for the repair of tissue defects.

In a first aspect, an embodiment of the present application provides a preparation method for a three-dimensional gelatin scaffold with interconnected pores. Referring to FIG. 1, which is a flow chart showing steps of a preparation method for a three-dimensional gelatin scaffold with interconnected pores according to an embodiment of the present application, the preparation method includes the following steps.

Step 1: a pharmaceutical gelatin is dissolved using a water bath heating method to obtain a gelatin solution at a preset concentration.

Step 2: the gelatin solution is emulsified using an ultrasonic crusher to obtain a gelatin emulsion.

Step 3: the gelatin emulsion is poured into a preset mold, and the gelatin emulsion is frozen and cured at −80° C. after being stabilized for a preset time, to obtain a cured product.

Step 4: vacuum drying is performed on the cured product using a low-temperature freeze dryer to obtain a dried product.

Step 5: the dried product is cross-linked and denatured with glutaraldehyde to obtain a cross-linked product.

Step 6: the cross-linked product is washed several times, followed by freeze-drying to obtain a three-dimensional gelatin scaffold with interconnected pores.

Figures 2, 3:
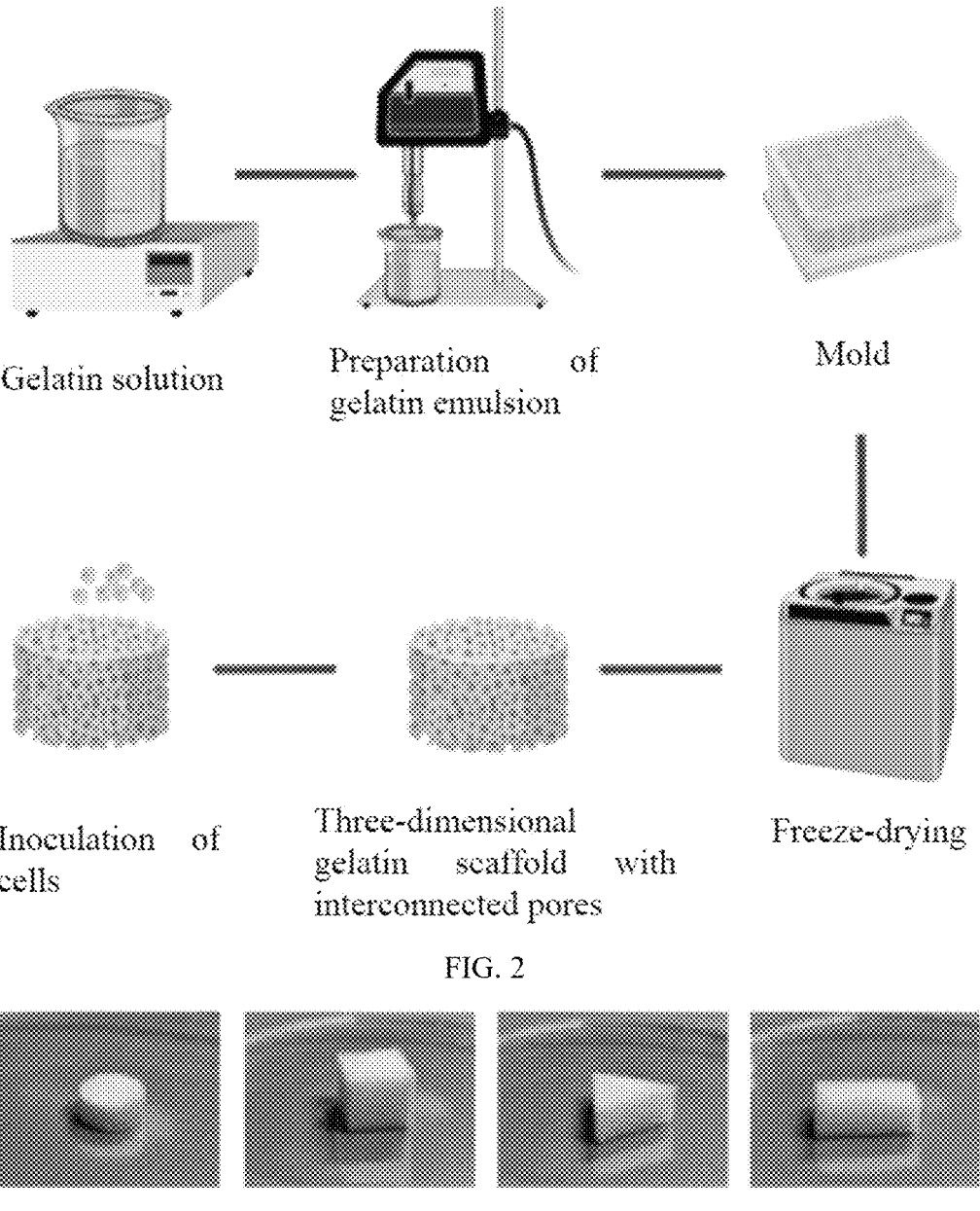
FIG. 2 is a flow chart showing the preparation method for a three-dimensional gelatin scaffold with interconnected pores according to an embodiment of the present application.
FIG. 3 is a schematic diagram showing three-dimensional gelatin scaffolds with interconnected pores of different shapes according to an embodiment of the present application.

The preparation method for a three-dimensional gelatin scaffold with interconnected pores is explained clearly in conjunction with FIG. 2, which is a flow chart showing the preparation method for a three-dimensional gelatin scaffold with interconnected pores according to an embodiment of the present application.

In implementing step 1, specifically, pharmaceutical gelatins at different concentrations are dissolved in a water bath to obtain a gelatin solution at a preset concentration. In the present application, the gelatin is swine-derived, the pharmaceutical gelatin has a Bloom strength of 250 Bloom/g, the preset concentration of the gelatin solution ranges from 2 wt % to 10 wt %, which in an embodiment of the present application may be selected as 2 wt %, 3 wt %, 4 wt %, 5 wt %, 6 wt %, 7 wt %, 8 wt %, 9 wt %, 10 wt %, etc., with the preferred preset concentration of the gelatin solution being 4 wt %.

In the process of preparing the three-dimensional gelatin scaffold with interconnected pores, the concentration of gelatin solution is crucial. In step 1, the preset concentration of the gelatin solution ranges from 2 wt % to 10 wt % due to the fact that excessively low concentration of gelatin solution is prone to collapsing an internal structure of the three-dimensional gelatin scaffold with interconnected pores, and excessively high concentration of gelatin solution is prone to the formation of gel, which is difficult for subsequent processing.

When water bath heating is performed in step 1, stirring time for dissolving the pharmaceutical gelatin ranges from 10 min to 40 min, and a stirring speed ranges from 100 rpm to 400 rpm. In an embodiment of the present application, the stirring time for dissolving may be selected as 10 min, 20 min, 30 min, 40 min, etc., and the stirring speed may be selected as 100 rpm, 200 rpm, 300 rpm, 400 rpm, etc.

In implementing step 2, specifically, the gelatin solution after being obtained is emulsified using the ultrasonic crusher to obtain the gelatin emulsion, with emulsification time being 30 s and an ultrasonic power set to 200 W.

In implementing step 3, specifically, to obtain three-dimensional gelatin scaffolds of different shapes and carry out industrial production, the gelatin emulsion is poured into the preset mold, and the gelatin emulsion is frozen and cured at −80° C. after being stabilized for a preset time, to obtain a cured product. The preset time for stabilizing the emulsion ranges from 1 min to 4 min, which, in an embodiment of the present application, may be selected as 1 min, 2 min, 3 min, 4 min, etc., with the preferred preset time for stabilizing the emulsion being 3 min. The preset mold may be in any shape, referring to FIG. 3, which is a schematic diagram showing three-dimensional gelatin scaffolds with interconnected pores of different shapes according to an embodiment of the present application. It can be seen that three-dimensional gelatin scaffolds with interconnected pores in cylindrical, square, three-dimensional triangular, rectangular shapes and other shapes can be obtained by the preset mold.

In the process of preparing the three-dimensional gelatin scaffold with interconnected pores, different stabilization times for gelatin emulsion affect the pore size, porosity and interconnected pores of a three-dimensional gelatin scaffold with interconnected pores. In addition, it is believed in related preparation methods that the pore size of the three-dimensional gelatin scaffold with interconnected pores tends to be larger as the stabilization time for gelatin emulsion increases.

Preferably, in this step, freeze-curing time for the cured product ranges from 3 h to 6 h, and the freeze-curing time may be selected as 3 h, 4 h, 5 h, 6 h, etc. In the preparation of three-dimensional gelatin scaffold with interconnected pores, reasonable freeze-curing time and conditions are crucial to the structural stability of three-dimensional gelatin scaffold with interconnected pores. Therefore, the optimal freeze-curing time results in a more structurally stable three-dimensional gelatin scaffold with interconnected pores. In an embodiment of the present application, the preferred freeze-curing time is 3 h.

In implementing step 4, specifically, after low-temperature curing, freeze-drying is performed on the cured product using the low-temperature freeze dryer to obtain a dried product. In step 4, the low-temperature freeze dryer for freeze-drying of the above cured product is a vacuum dryer, and in this step, it is necessary to ensure that a vacuum strength of the freeze-drying is not greater than 10 Pa, i.e., it is necessary to ensure that the vacuum strength shown on the display of the vacuum dryer is not greater than 10 Pa. The vacuum drying time ranges from 24 h to 72 h, which may be selected as 24 h, 36 h, 48 h, 60 h and 72 h. In step 4, the reason for vacuum drying is that the vacuum environment can reduce the pressure around the material, allowing ice crystals to change directly from a solid to a gaseous state, and allowing the ice crystals to be removed to form a stable porous structure.

In implementing step 5, specifically, the dried product is cross-linked and denatured with glutaraldehyde to obtain the cross-linked product. In an embodiment of the present application, glutaraldehyde at a concentration of 0.25% is preferred for cross-linking and denaturation due to the fact that gelatin is unstable in vivo, and insufficient cross-linking is prone to dissolving and disintegrating the obtained three-dimensional gelatin scaffold with interconnected pores, and excessive cross-linking results in cross-linking agent residing in the obtained three-dimensional gelatin scaffold with interconnected pores, and it is difficult to remove the residual cross-linking agent.

In implementing step 6, specifically, anhydrous ethanol and distilled water are employed to wash the cross-linked product several times to remove the residual cross-linking agent, the number of times of washing is greater than or equal to 10, and the time for each washing is greater than or equal to 1 h, and after washing, the cross-linked product is subjected to freeze-drying to obtain the three-dimensional gelatin scaffold with interconnected pores.

In an alternative embodiment of the present application, after the three-dimensional gelatin scaffold with interconnected pores is obtained, the preparation method further includes that according to the shapes of the tissues that need to be filled and repaired, the three-dimensional gelatin scaffold with interconnected pores is cut into different shapes and sizes, so that the scaffold can be applicable to the filling and repair of different types of tissue defects.

In an alternative embodiment of the present application, after the three-dimensional gelatin scaffold with interconnected pores is obtained, the preparation method further includes that the three-dimensional gelatin scaffold with interconnected pores is irradiated and sterilized using cobalt 60 (Co 60) to investigate the effect of different pore sizes, porosities, and interconnected pores of the scaffold on the adhesion, survival, and proliferation behavior of the stem cells. The stem cells include adipose-derived mesenchymal stem cells, bone marrow mesenchymal stem cells or umbilical cord mesenchymal stem cells.

The present application provides a preparation method for a three-dimensional gelatin scaffold with interconnected pores, specifically involves that a pharmaceutical gelatin is dissolved using a water bath heating method to obtain a gelatin solution at a preset concentration; the gelatin solution is emulsified using an ultrasonic crusher to obtain a gelatin emulsion; the gelatin emulsion is poured into a preset mold, and the gelatin emulsion is cured by freezing at −80° C. after being stabilized for a preset time, to obtain a cured product; vacuum drying is performed on the cured product using a low-temperature freeze dryer to obtain a dried product; the dried product is cross-linked and denatured with glutaraldehyde to obtain a cross-linked product; and the cross-linked product is washed several times, followed by freeze-drying to obtain a three-dimensional gelatin scaffold with interconnected pores. The three-dimensional gelatin scaffold with interconnected pores, which has an optimal pore size and porosity, can be obtained by the preparation method mentioned above. The preparation method mentioned above is simple, stable and efficient, and is applicable to industrial production. The novel three-dimensional scaffold with interconnected pores prepared in the present application has pore size, porosity, and interconnected pores that are appropriate for loading stem cells. The three-dimensional gelatin scaffold with interconnected pores shows excellent hemostatic properties, and is suitable as a platform for loading adipose-derived mesenchymal stem cells for the regeneration and repair of tissue defects.

In a second aspect, an embodiment of the present application provides an application of a three-dimensional gelatin scaffold with interconnected pores in preparing a scaffold for tissue defect repair, a three-dimensional gelatin scaffold with interconnected pores being obtained by the preparation method mentioned in the first aspect, and the three-dimensional gelatin scaffold with interconnected pores being used as a carrier for stem cells for tissue defect repair, such as skin repair, bone repair, and intervertebral disc repair.

In an alternative embodiment of the present application, the stem cells include adipose-derived mesenchymal stem cells, bone marrow mesenchymal stem cells or umbilical cord mesenchymal stem cells. The adipose-derived mesenchymal stem cells are extracted from the fat of a groin area, which is rich in content and easy to separate, and the influence of connective tissue and red blood cells on cell extraction can be effectively avoided.

In an alternative embodiment of the present application, the three-dimensional gelatin scaffold with interconnected pores is cut into different shapes and sizes for regeneration and repair of tissue defects of different shapes.

In an alternative embodiment of the present application, the three-dimensional gelatin scaffold with interconnected pores has a pore size ranging from 70 μm to 450 μm, a porosity ranging from 64.2% to 97.7%, and a pore size of interconnected pores ranging from 30 μm to 185 μm.

The three-dimensional gelatin scaffold with interconnected pores prepared by the preparation method can be used for regeneration and repair of tissue defects combined with stem cells (taking adipose-derived mesenchymal stem cells as an example). The technical solutions provided by the present application are described in detail below in connection with the embodiments, but the embodiments cannot to be construed as limiting the scope of protection of the present application.

Embodiment 1: A Preparation Method for a Three-Dimensional Gelatin Scaffold with Interconnected Pores Specifically, the preparation method for a three-dimensional gelatin scaffold includes the following steps:

Step 1: 500 mL of deionized water was added into a 1000 mL glass beaker, and 3 g of gelatin was weighted with weighing paper. The gelatin was added into the deionized water, followed by heating and stirring continuously under 60° C. water bath, allowing a gelatin solution to be uniform and transparent, and the gelatin solution at a concentration of 6 wt % was obtained.

Step 2: the gelatin solution was emulsified ultrasonically, and a gelatin emulsion was obtained until the solution became a homogeneous emulsion and a volume thereof was increased to 2 to 3 times of an original volume.

Step 3: the gelatin emulsion was quickly transferred into a pre-cooled mold, the gelatin emulsion was stabilized for 3 min, and the stabilized gelatin emulsion was rapidly transferred to a −80° C. freezer for freeze-curing for 3 h to obtain a cured product.

Step 4: the cured product was transferred to a vacuum freeze dryer for vacuuming for 20 min until a vacuum strength was not more than 10 Pa, and continuous freeze-drying was performed for 24 h to obtain a dried product.

Step 5: the dried product was cross-linked and denatured with glutaraldehyde to obtain a cross-linked product.

Step 6: the cross-linked product was soaked in anhydrous ethanol and distilled water for washing several times, and after secondary freeze-drying, a three-dimensional gelatin scaffold with interconnected pores was obtained, which was stored for later use.

Embodiment 2-Embodiment 5

The concentration of gelatin solution is crucial to the preparation of the three-dimensional gelatin scaffold with interconnected pores due to the fact that excessively low concentration of gelatin solution is prone to collapsing the prepared three-dimensional gelatin scaffold with interconnected pores, failing to be applied practically, and excessively high concentration of gelatin solution is prone to the formation of a gel, which is difficult for subsequent processing.

To obtain the optimal concentration of gelatin solution, in Embodiment 2-Embodiment 5, the concentration of gelatin solution was changed to 2 wt %, 4 wt %, 8 wt %, and 10 wt %, and three-dimensional gelatin scaffolds with interconnected pores were separately prepared according to the preparation method of Embodiment 1.

Embodiment 6: A Preparation Method for a Three-Dimensional Gelatin Scaffold with Interconnected Pores Different stabilization times for gelatin emulsion affect the pore size, porosity and interconnected pores of a three-dimensional gelatin scaffold with interconnected pores. A shorter stabilization time for gelatin emulsion results in a smaller pore size of the three-dimensional gelatin scaffold with interconnected pores, and a longer stabilization time for gelatin emulsion results in a larger pore size of the three-dimensional gelatin scaffold with interconnected pores. To obtain an optimal stabilization time for gelatin emulsion, the stabilization time for gelatin emulsion was changed to 1 min, and a three-dimensional gelatin scaffold with interconnected pores was prepared according to the method of Embodiment 1.

Embodiment 7-Embodiment 10

According to the stabilization time for gelatin emulsion in Embodiment 6, in Embodiment 7-Embodiment 11, the concentration of gelatin solution was changed to 2 wt %, 4 wt %, 8 wt %, and 10 wt %, and three-dimensional gelatin scaffolds with interconnected pores were separately prepared according to the preparation method of Embodiment 1.

Embodiment 11: A Preparation Method for a Three-Dimensional Gelatin Scaffold with Interconnected Pores Different stabilization times for gelatin emulsion affect the pore size, porosity and interconnected pores of a three-dimensional gelatin scaffold with interconnected pores. A shorter stabilization time for gelatin emulsion results in a smaller pore size of the three-dimensional gelatin scaffold with interconnected pores, and a longer stabilization time for gelatin emulsion results in a larger pore size of the three-dimensional gelatin scaffold with interconnected pores. To obtain an optimal stabilization time for gelatin emulsion, the stabilization time for gelatin emulsion was changed to 2 min, and a three-dimensional gelatin scaffold with interconnected pores was prepared according to the method of Embodiment 1.

Embodiment 12-Embodiment 15

According to the stabilization time for gelatin emulsion in Embodiment 11, in Embodiment 12-Embodiment 15, the concentration of gelatin solution was changed to 2 wt %, 4 wt %, 8 wt %, and 10 wt %, and three-dimensional gelatin scaffolds with interconnected pores were separately prepared according to the preparation method of Embodiment 1.

Embodiment 16: A Preparation Method for a Three-Dimensional Gelatin Scaffold with Interconnected Pores Different stabilization times for gelatin emulsion affect the pore size, porosity and interconnected pores of a three-dimensional gelatin scaffold with interconnected pores. A shorter stabilization time for gelatin emulsion results in a smaller pore size of the three-dimensional gelatin scaffold with interconnected pores, and a longer stabilization time for gelatin emulsion results in a larger pore size of the three-dimensional gelatin scaffold with interconnected pores. To obtain an optimal stabilization time for gelatin emulsion, the stabilization time for gelatin emulsion was changed to 4 min, and a three-dimensional gelatin scaffold with interconnected pores was prepared according to the method of Embodiment 1.

Embodiment 17-Embodiment 20

According to the stabilization time for gelatin emulsion in Embodiment 16, in Embodiment 17-Embodiment 20, the concentration of gelatin solution was changed to 2 wt %, 4 wt %, 8 wt %, and 10 wt %, and three-dimensional gelatin scaffolds with interconnected pores were separately prepared according to the preparation method of Embodiment 1.

Embodiment 21: Morphological Characterization of a Three-Dimensional Gelatin Scaffold with Interconnected Pores The morphology, the pore size, the porosity and the pore size of the interconnected pores of the three-dimensional gelatin scaffold with interconnected pores prepared in Embodiments 1 to 20 were observed by a stereo microscope and a scanning electron microscope.

The procedure for observing the three-dimensional gelatin scaffold with interconnected pores using the stereo microscope was as follows. The three-dimensional gelatin scaffold with interconnected pores in the above embodiment was cut into a cylinder with a radius of 4 mm and a height of 3 mm, and the cylinder was placed in a culture dish, and then was transferred to a sample stage of the stereo microscope. A color of a background plate was selected. A light source was turned on and a brightness and angle of the light source were adjusted. The sample was observed through ocular lens, and a focus was adjusted until the sample could be seen clearly, and a picture was shot and stored. The results are shown in FIG. 4.

The procedure for observing the three-dimensional gelatin scaffold with interconnected pores using the scanning electron microscope was as follows. The three-dimensional gelatin scaffold with the interconnected pores in the above embodiment was cut into thin slices (6×6×2 mm), which were adhered to a sample stage with conductive adhesive, and it was ensured that the samples were dry and clean. Sample surfaces were sprayed with gold and analyzed by the scanning electron microscope, and the pore size was further analyzed by Image-J software. The results are shown in FIG. 5.

The process of determining the porosity of the three-dimensional gelatin scaffold with interconnected pores was as follows. A gelatin sponge was cut into a rectangle (6×6×8 mm), and the water in the sponge was squeezed out. The sponge was dried and weighed, and the weight was recorded as W1. The weighed sponge was soaked in anhydrous ethanol for 30 min, and then taken out and weighted, and the weight was recorded as W2. The formula for calculating the porosity is as follows: $P (\%)=(W2-W1)/\rho V \times 100\%$, where P is the porosity, $\rho$ is the density of anhydrous ethanol, and V is a volume of the gelatin sponge.

Figure 4:
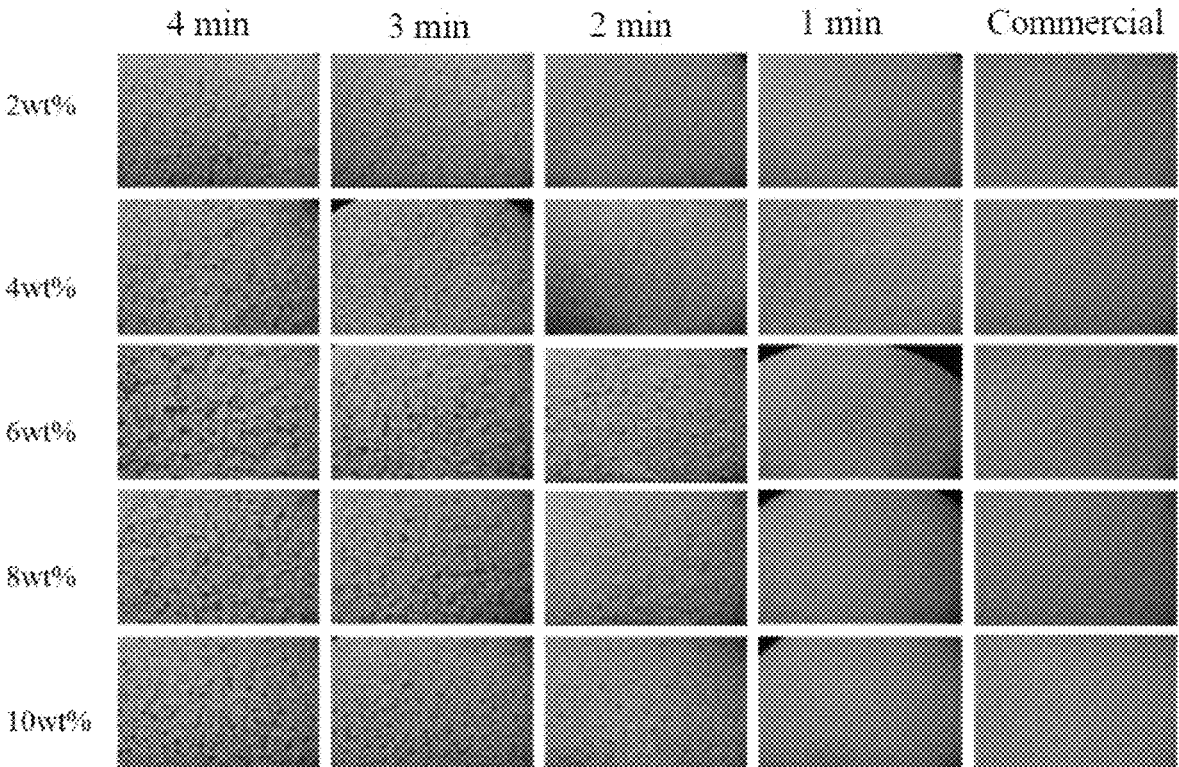
FIG. 4 is a diagram from stereo microscope, showing different three-dimensional gelatin scaffolds with interconnected pores according to an embodiment of the present application.
Figure 5:
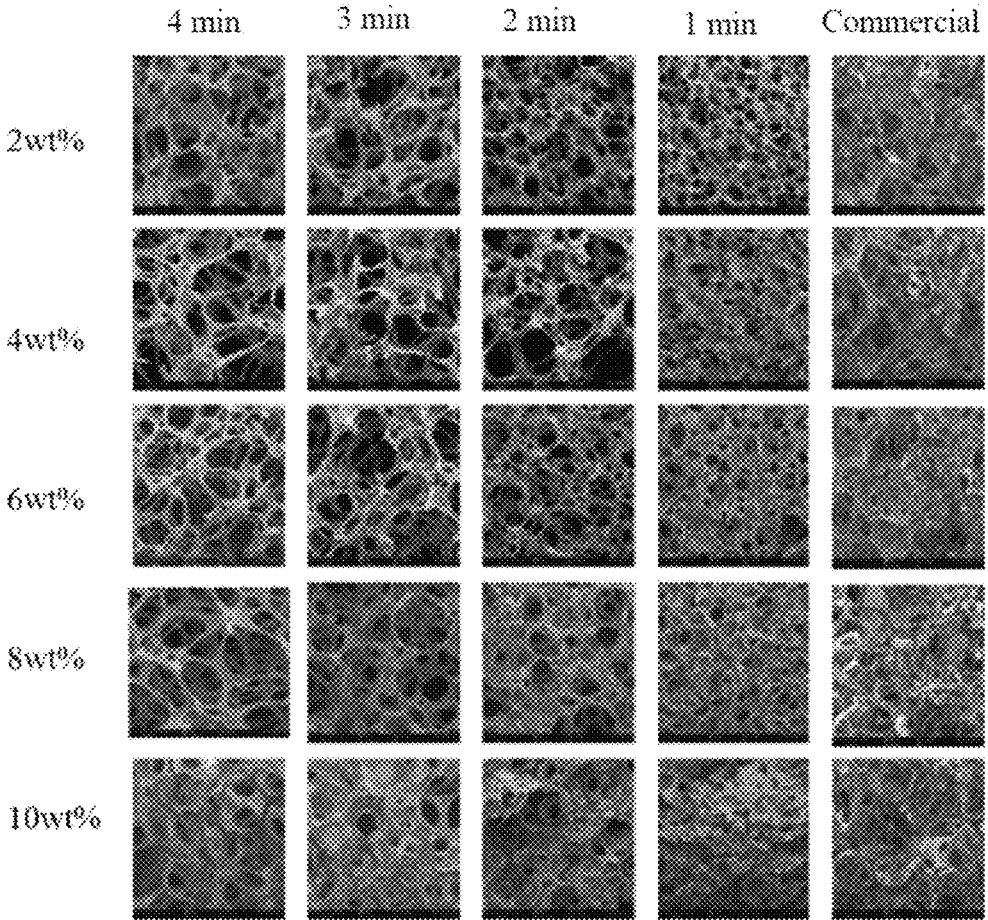
FIG. 5 is a diagram from scanning electron microscope, showing different three-dimensional gelatin scaffolds with interconnected pores according to an embodiment of the present application.

As can be seen in FIGS. 4 and 5, compared with the control group (commercial gelatin, abbreviated as commercial in the figure), as the concentration of gelatin solution increases, the pore size of the three-dimensional gelatin scaffold with interconnected pores tends to decrease but is not significant, and as the stabilization time for gelatin emulsion increases, the pore size of the three-dimensional gelatin scaffold with interconnected pores increases significantly.

Figure 6:
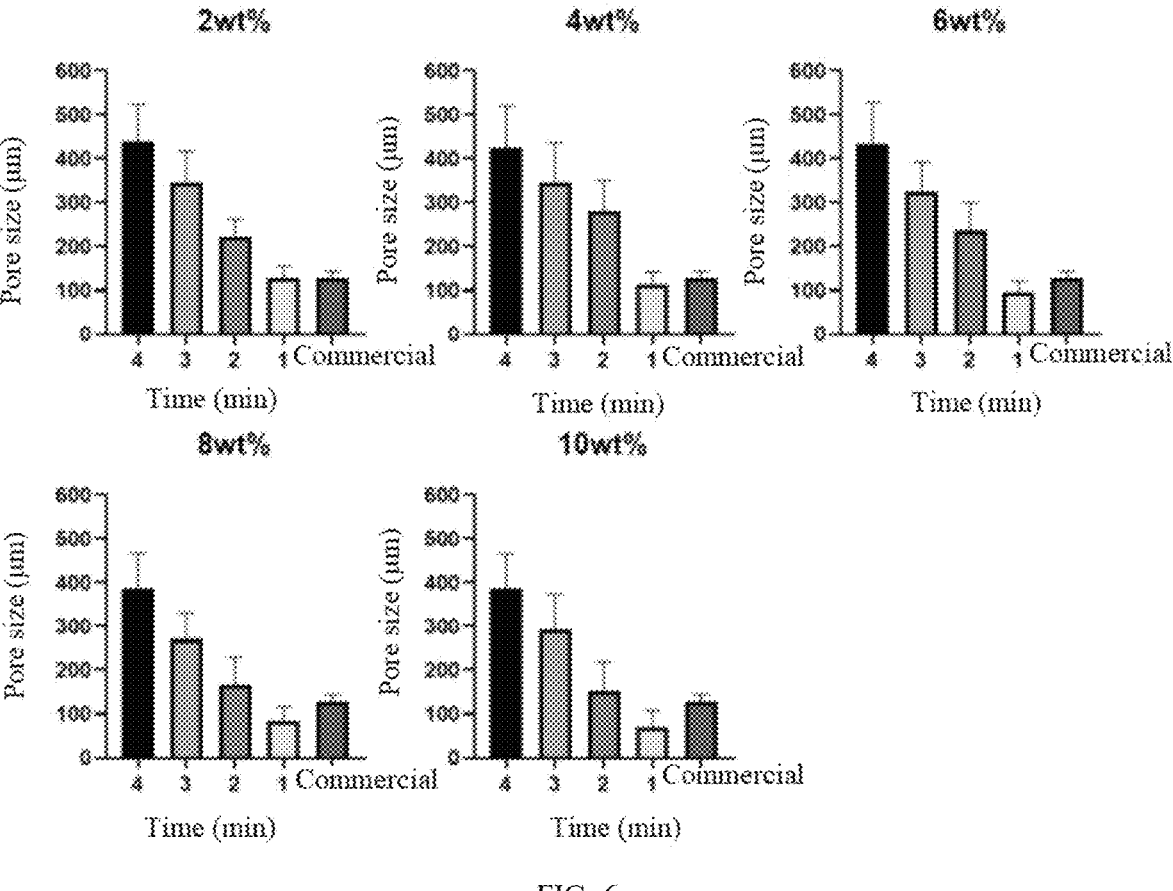
FIG. 6 is a result diagram showing pore sizes of different three-dimensional gelatin scaffolds with interconnected pores according to an embodiment of the present application.

Specific pore size results are shown in FIG. 6, sequentially exhibiting the pore sizes of the three-dimensional gelatin scaffolds with interconnected pores prepared at different gelatin emulsion stabilization times (4 min, 3 min, 2 min and 1 min) in a case that the concentrations of gelatin solution are 2 wt %, 4 wt %, 6 wt %, 8 wt % and 10 wt %. In a case that the concentration of gelatin solution is 2 wt %, as the stabilization time for gelatin emulsion is changed from 4 min to 1 min, the corresponding pore size of the three-dimensional gelatin scaffold with interconnected pores is reduced from 435 μm to 125 μm. In a case that the concentration of gelatin solution is 4 wt %, as the stabilization time for gelatin emulsion is changed from 4 min to 1 min, the corresponding pore size of the three-dimensional gelatin scaffold with interconnected pores is reduced from 425 μm to 112 μm. In a case that the concentration of gelatin solution is 6 wt %, as the stabilization time for gelatin emulsion is changed from 4 min to 1 min, the corresponding pore size of the three-dimensional gelatin scaffold with interconnected pores is reduced from 430 μm to 100 μm. In a case that the concentration of gelatin solution is 8 wt %, as the stabilization time for gelatin emulsion is changed from 4 min to 1 min, the corresponding pore size of the three-dimensional gelatin scaffold with interconnected pores is reduced from 390 μm to 90 μm. In a case that the concentration of gelatin solution is 10 wt %, as the stabilization time for gelatin emulsion is changed from 4 min to 1 min, the corresponding pore size of the three-dimensional gelatin scaffold with interconnected pores is reduced from 370 μm to 70 μm. The pore size in the control group is only 130.522±34.16 μm. These pore size results indicate that the pore size tends to increase as the stabilization time for gelatin emulsion is prolonged.

Figure 7:
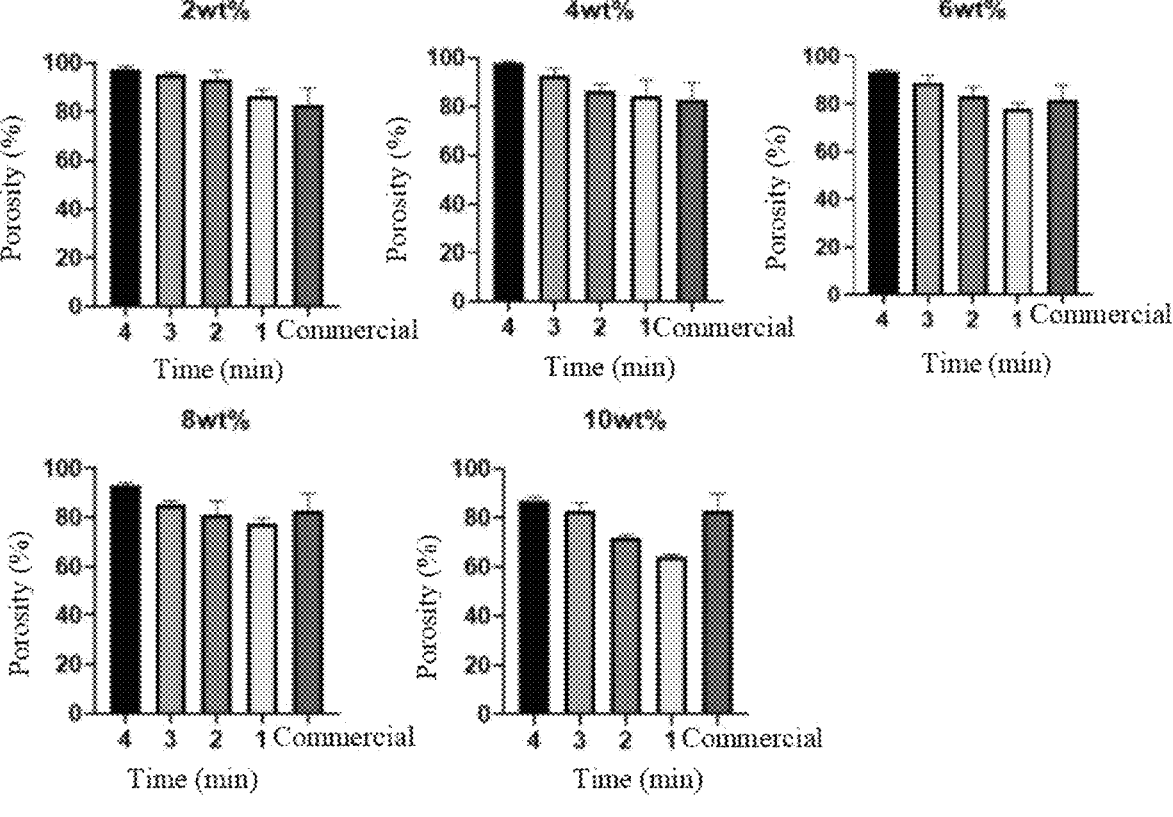
FIG. 7 is a result diagram showing porosities of different three-dimensional gelatin scaffolds with interconnected pores according to an embodiment of the present application.

The specific porosity results are shown in FIG. 7, sequentially exhibiting the porosities of the three-dimensional gelatin scaffolds with interconnected pores prepared at different stabilization times (4 min, 3 min, 2 min, and 1 min) in a case that the concentrations of gelatin solutions are 2 wt %, 4 wt %, 6 wt %, 8 wt %, and 10 wt %. In a case that the concentration of gelatin solution is 2 wt %, as the stabilization time for gelatin emulsion is changed from 4 min to 1 min, the corresponding porosity of the three-dimensional gelatin scaffold with interconnected pores is reduced from 97.7% to 86.2%. In a case that the concentration of gelatin solution is 4 wt %, as the stabilization time for gelatin emulsion is changed from 4 min to 1 min, the corresponding porosity of the three-dimensional gelatin scaffold with interconnected pores is reduced from 97.2% to 84.2%. In a case that the concentration of gelatin solution is 6 wt %, as the stabilization time for gelatin emulsion is changed from 4 to 1 min, the corresponding porosity of the three-dimensional gelatin scaffold with interconnected pores is reduced from 94.7% to 78.1%. In a case that the concentration of gelatin solution is 8 wt %, as the stabilization time for gelatin emulsion is changed from 4 min to 1 min, the corresponding porosity of the three-dimensional gelatin scaffold with interconnected pores is reduced from 94.2% to 78.3%. In a case that the concentration of gelatin solution is 10 wt %, as the stabilization time for gelatin emulsion is changed from 4 min to 1 min, the corresponding porosity of the three-dimensional gelatin scaffold with interconnected pores is reduced from 86.7% to 64.2%. The porosity in the control group (commercial gelatin, abbreviated as commercial in the figure) is only 78.6%. These porosity results indicate that the porosity tends to increase as the stabilization time for gelatin emulsion is prolonged.

Figure 8:
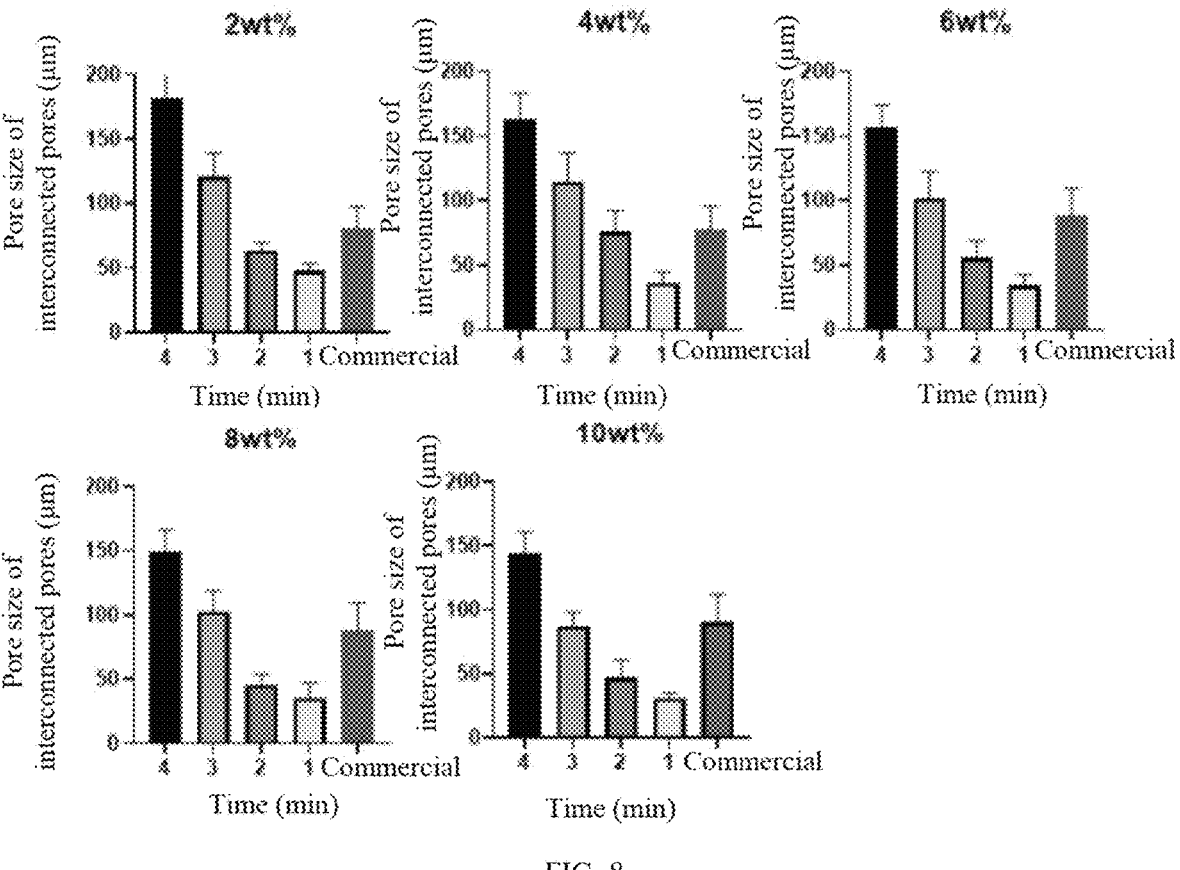
FIG. 8 is a result diagram showing pore sizes of interconnected pores of different three-dimensional gelatin scaffolds with interconnected pores according to an embodiment of the present application.

Specific pore size results of the interconnected pores are shown in FIG. 8, sequentially exhibiting the pore sizes of the interconnected pores of the three-dimensional gelatin scaffolds with interconnected pores prepared at different stabilization times (4 min, 3 min, 2 min, and 1 min) in a case that the concentrations of gelatin solutions are 2 wt %, 4 wt %, 6 wt %, 8 wt %, and 10 wt %. In a case that the concentration of gelatin solution is 2 wt %, as the stabilization time for gelatin emulsion is changed from 4 min to 1 min, the corresponding pore size of interconnected pores is reduced from 185 μm to 50 μm. In a case that the concentration of gelatin solution is 4 wt %, as the stabilization time for gelatin emulsion is changed from 4 min to 1 min, the corresponding pore size of interconnected pores is reduced from 160 μm to 36 μm. In a case that the concentration of gelatin solution is 6 wt %, as the stabilization time for gelatin emulsion is changed from 4 min to 1 min, the corresponding pore size of interconnected pores is reduced from 155 μm to 36 μm. In a case that the concentration of gelatin solution is 8 wt %, as the stabilization time for gelatin emulsion is changed from 4 min to 1 min, the corresponding pore size of interconnected pores is reduced from 150 μm to 35 μm. In a case that the concentration of gelatin solution is 10 wt %, as the stabilization time for gelatin emulsion is changed from 4 min to 1 min, the corresponding pore size of interconnected pores is reduced from 140 μm to 30 μm. The pore size of the interconnected pore in the control group (commercial gelatin, abbreviated as commercial in the figure) is 90.15±5.426 μm. Those results for the pore size of the interconnected pores indicate that the pore size of the interconnected pores tends to increase as the stabilization time for gelatin emulsion is prolonged.

From the above characterization results, it can be seen that in the above preparation method, the optimal concentration of gelatin solution is 4 wt %, and the optimal stabilization time for gelatin emulsion is 3 min. The three-dimensional gelatin scaffold with interconnected pores prepared under these conditions has a pore size of 341.671±51.82 μm, a porosity of 96.2±4%, and a pore size of the interconnected pores of 110.56±5.957 μm. The pore size, porosity and pore size of the interconnected pore of the three-dimensional gelatin scaffold with interconnected pores prepared under these conditions are much better than those of the control group, indicating that the three-dimensional gelatin scaffold with interconnected pores prepared in the present application are obviously better than the commercial products, and the above preparation method is simple and favorable for industrial production. The three-dimensional gelatin scaffold with interconnected pores prepared under these conditions are subjected to cell loading experiments and tissue defect repair experiments.

Embodiment 22: Experiment for Loading Adipose-Derived Mesenchymal Stem Cells by Three-Dimensional Gelatin Scaffold with Interconnected Pores A three-dimensional gelatin scaffold with interconnected pores prepared under the condition of 4 wt % concentration of gelatin solution and stabilization time of 3 min was selected for loading stem cells, and adipose-derived mesenchymal stem cells were used as the loaded stem cells for the experiment. The specific steps were shown as follows:

Step 1: in this embodiment, for easy inoculation and loading of adipose-derived mesenchymal stem cells, the three-dimensional gelatin scaffold with interconnected pores was cut into a cylinder with a diameter of 8 μm and a height of 4 μm. The cylinder was sealed, and then irradiated and sterilized by cobalt 60, to obtain a sterile three-dimensional gelatin scaffold with interconnected pores.

Step 2: the sterile three-dimensional gelatin scaffold with interconnected pores was soaked in a 48-well plate of a serum-free Dulbecco's modified eagle medium (DMEM, containing various amino acids and glucose) for fully rehydrating for 2 h.

Step 3: the medium was removed with a 1 mL pipette gun, and a medium containing 10% fetal bovine serum (FBS) was added, followed by incubating in a constant-temperature incubator containing 5% $CO_2$ at 37° C. for 30 min.

Step 4: the pre-cultured adipose-derived mesenchymal stem cells were digested and counted to prepare a cell suspension at a concentration of $1\times10^5$/mL, and the medium was removed from the 48-well plate. $1\times10^4$ cells were inoculated uniformly in each well on the surface of the three-dimensional gelatin scaffold with interconnected pores, followed by incubating in the constant-temperature incubator for 2 h to accelerate cell adhesion.

Step 5: the 48-well plate was taken out after 2 h, and each well was replenished with 500 μL of medium containing 10% serum, followed by continuous incubation and regular observation.

After loading the stem cells, cell proliferation ability was determined by cell counting kit-8 (CCK-8) method, and the result was used as the characterization result of loading adipose-derived mesenchymal stem cells by the three-dimensional gelatin scaffold with interconnected pores. The specific operation method was as follows. The well-grown adipose-derived mesenchymal stem cells were inoculated on the surface of the scaffold, and the medium was completely removed at specific times (1, 3 and 5 days). 200 μL of medium containing 10% CCK-8 working solution (without serum) was added to each well, and the cells were incubated in a constant-temperature incubator for 2 h. 100 μL of liquid was pipetted from each well and transferred to a 96-well plate, and an absorbance value of each well was detected by an enzyme meter (at a wavelength of 450 nm).

Figure 9:
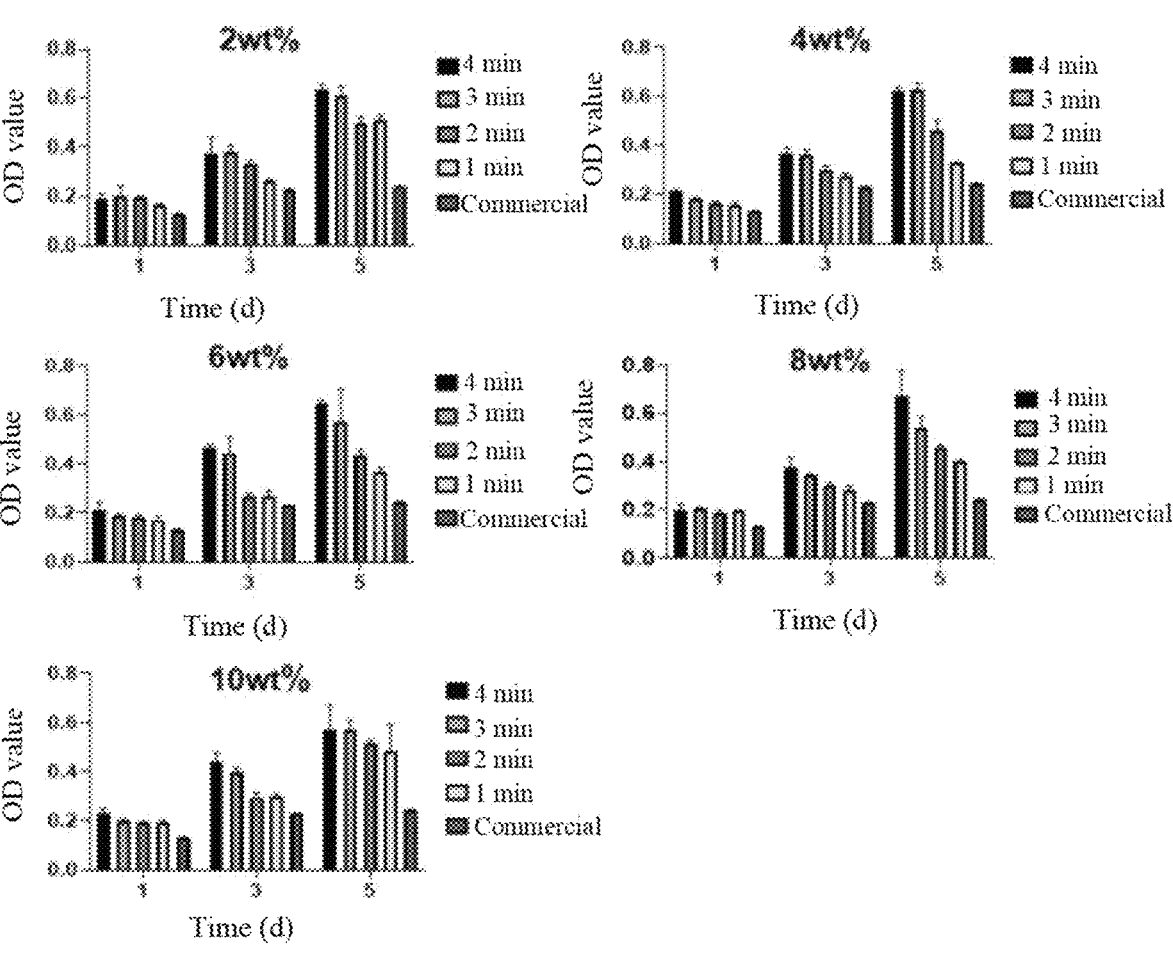
FIG. 9 is a result diagram showing the effect of different three-dimensional gelatin scaffolds with interconnected pores on cell proliferation ability according to an embodiment of the present application.

The results of the CCK-8 are shown in FIG. 9. FIG. 9 indicates that the OD value of each experimental group is significantly increased with prolonged culture time and is higher than that of the control group (commercial gelatin, abbreviated as commercial in the figure), suggesting that the three-dimensional gelatin scaffold with interconnected pores prepared by the aforementioned method in the first aspect is suitable for the growth of adipose-derived mesenchymal stem cells. Additionally, the overall effect of the scaffold loaded with stem cells is superior to that of the control group. The OD values of the three-dimensional gelatin scaffold with interconnected pores at 3 min and 4 min are significantly higher than those of the scaffold at 1 min and 2 min, demonstrating that, to a certain extent, large pores provide sufficient growth space for cell growth and nutrients delivery, facilitating cell proliferation, and the interconnected pores with large pore size provide channels for cell migration, promoting cell proliferation. By comprehensive observation of the cell proliferation ability on gelatin scaffolds prepared under different conditions, it is found that the three-dimensional gelatin scaffold with interconnected pores prepared under the conditions of a concentration of gelatin solution of 4 wt % and an emulsion stabilization time of 3 min has a pore size of 341.671±51.82 μm, a porosity of 96.2±4%, and a pore size of interconnected pores of 110.56±5.957 μm, and the gelatin scaffold prepared under this condition is most favorable for the proliferation of adipose-derived mesenchymal stem cells. Therefore, this preparation condition serves as the preferred process for the preparation of scaffolds for tissue defect repair and used for studies on effect of in vivo tissue defect repair.

Figure 10A:
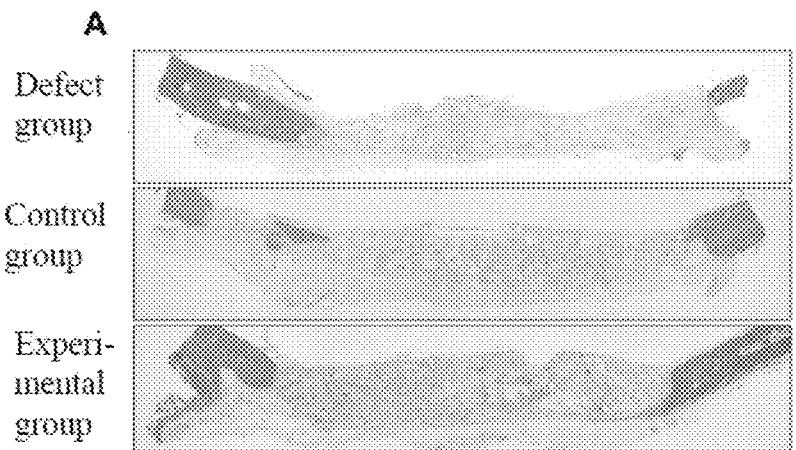
FIG. 10A shows the hematoxylin-eosin (HE) staining effect of a three-dimensional gelatin scaffold with interconnected pores on the repair of tissue defects according to an embodiment of the present application.
Figure 10B:
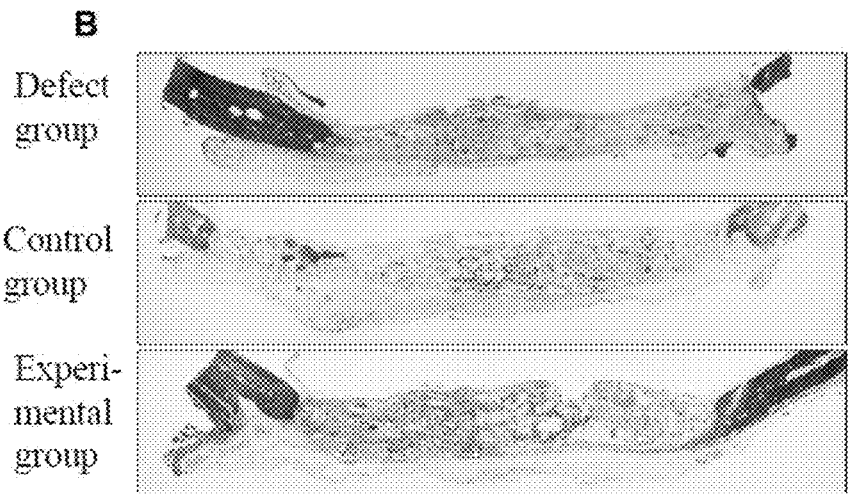
FIG. 10B shows the Masson's trichrome staining effect of a three-dimensional gelatin scaffold with interconnected pores on the repair of tissue defects according to an embodiment of the present application.

Embodiment 23: Effect of a Three-Dimensional Gelatin Scaffold with Interconnected Pores on the Tissue Defect Repair In this embodiment, a cranial repair model was employed to evaluate the repair effect of three-dimensional gelatin scaffold with interconnected pores loaded with adipose-derived mesenchymal stem cells on tissue defects. The specific operational process was as follows. After anesthetizing the rats, they were fixed on a surgical table in a prone position. The fur was shaved, and the skin was disinfected. A scalp was incised longitudinally with an incision of 10 mm, and blunt dissection was performed on skin tissues and periosteum to fully expose cranial bone tissues. An abrasion drill was used to circularly cut a cranial bone of 6 mm in diameter, successfully constructing a cranial defect model. Control group: a gelatin sponge pre-inoculated with adipose-derived mesenchymal stem cells was transplanted into a cranial defect area. Experimental group: a three-dimensional gelatin scaffold with interconnected pores pre-inoculated with adipose-derived mesenchymal stem cells was transplanted into a cranial defect area. Four weeks after surgery, the rats were euthanized, and cranial bone tissues were obtained. The cranial bone samples were subjected to routine decalcification, followed by paraffin embedding and sectioning. The repair effects of the cranial defect models in each group were observed using HE staining and Masson's trichrome staining. The experimental results are shown in FIGS. 10A-10B. FIG. 10A shows the HE staining results and FIG. 10B shows the Masson's staining results. The experimental groups are as follows: defect group (simple cranial defect model), control group (commercial gelatin loaded with adipose-derived mesenchymal stem cells), and experimental group (three-dimensional gelatin scaffold with interconnected pores loaded with adipose-derived mesenchymal stem cells).

FIG. 10A shows that in the simple cranial defect group, the boundary of the cranial defect area is clearly defined, and the defect area is filled with fibrous tissues. In the control group, the boundary of the cranial defect area is clearly defined, and the defect area is filled with fibrous tissues, and some nondegraded gelatin sponge materials are still visible within the fibrous tissues. In the experimental group, the boundary of the cranial defect area is blurred, and the defect area is filled with fibrous tissues, and a small quantity of nondegraded gelatin scaffold materials are visible within the fibrous tissues.

FIG. 10B shows that in the simple cranial defect group, the defect area is filled with tissues primarily including fibrous tissues, with a small amount of bone tissue deposition. In the control group, the defect area is filled with tissues mainly including fibrous tissues, with a small amount of bone tissue deposition. In the experimental group, the tissues filling the cranial defect area are primarily fibrous tissues, but there is a substantial amount of bone tissue deposition within the fibrous tissues, and the boundary of the cranial defect area is blurred.

The above staining results reveal that, compared with the control group and the defect group, the three-dimensional gelatin scaffold with interconnected pores prepared in the present application after loading adipose-derived mesenchymal stem cells has a better repair effect on cranial bone defects.

The preparation method for a three-dimensional gelatin scaffold with interconnected pores and an application thereof provided in the present application are described in detail above, and specific examples are used herein to illustrate the principles and implementation of the present application. The illustrations of the above embodiments merely serve for assisting in the understanding of the method and the core idea of the present application. At the same time, for those ordinary skilled in the art, according to the ideas of the present application, there may be changes in the specific implementation and the scope of application. In summary, the contents of this specification are not to be interpreted as a limitation of the present application.

The invention claimed is:

1. A preparation method for a three-dimensional gelatin scaffold with interconnected pores, comprising:
   step 1: dissolving a pharmaceutical gelatin with a 250 Bloom/g of Bloom strength using a water bath heating method to obtain a gelatin solution at a preset concentration of 2 wt %-5 wt % or 7 wt %-10 wt %;
   step 2: emulsifying the gelatin solution using an ultrasonic crusher to obtain a gelatin emulsion, with emulsification time being 30 s and an ultrasonic power set to 200 W;
   step 3: pouring the gelatin emulsion into a preset mold, and after the gelatin emulsion being laid for a preset time of 1 min to 4 min, performing an operation of freezing and curing on the gelatin emulsion at −80° C., to obtain a cured product;
   step 4: performing vacuum drying of the cured product using a freeze dryer to obtain a dried product;
   step 5: cross-linking and denaturing the dried product with glutaraldehyde to obtain a cross-linked product;
   step 6: washing the cross-linked product several times, followed by freeze-drying to obtain a three-dimensional gelatin scaffold with interconnected pores; and
   step 7: irradiating and sterilizing the three-dimensional gelatin scaffold with interconnected pores by using cobalt 60 to investigate the effect of different pore sizes, porosities, and interconnected pores of the scaffold on the adhesion, survival, and proliferation behavior of stem cells;
   wherein: in step 1, stirring time for dissolving the pharmaceutical gelatin ranges from 10 min to 40 min, and a stirring speed for dissolving the pharmaceutical gelatin ranges from 100 rpm to 400 rpm; in step 3, time for the operation of freezing and curing ranges from 3 h to 6 h; and in step 4, a vacuum strength for vacuum drying of the cured product using the freeze dryer is not greater than 10 Pa, and vacuum drying time ranges from 24 h to 72 h.

* * * * *